United States Patent [19]

Schwartz

[11] Patent Number: 5,016,641
[45] Date of Patent: May 21, 1991

[54] SPECTRAL INTERPOLATION OF ULTRASOUND DOPPLER SIGNAL

[75] Inventor: Gary Schwartz, Seattle, Wash.

[73] Assignee: Advanced Technology Laboratories, Inc., Bothell, Wash.

[21] Appl. No.: 435,077

[22] Filed: Nov. 13, 1989

[51] Int. Cl.⁵ .............................................. A61B 8/00
[52] U.S. Cl. ........................... 128/661.09; 128/661.05; 73/861.25
[58] Field of Search ...................... 128/661.09, 661.05; 73/861.25

[56] References Cited

U.S. PATENT DOCUMENTS

| | | | |
|---|---|---|---|
| 4,052,977 | 10/1977 | Kay | 128/661.07 |
| 4,559,952 | 12/1985 | Angelsen et al. | 128/661.09 |
| 4,680,739 | 7/1987 | Lannuzel | 128/661.09 X |
| 4,817,617 | 4/1989 | Takeuchi et al. | 128/661.09 X |
| 4,817,618 | 4/1989 | Des Jardins et al. | 128/661.09 |
| 4,848,354 | 7/1989 | Angelsen et al. | 128/661.09 X |
| 4,930,514 | 6/1990 | Baba et al. | 128/661.09 |
| 4,934,373 | 6/1990 | Angelsen et al. | 128/661.09 |

*Primary Examiner*—Francis Jaworski

[57] ABSTRACT

A method and apparatus for producing the Doppler audio output in a medical ultrasound system. The system includes a transmitter for transmitting ultrasound into a body, a receiver for receiving and processing echoes to produce a Doppler signal, and a Doppler signal processor for converting the Doppler signals into an audio signal that in turn is converted into audible sound. The system alternates between first time intervals during which the Doppler samples are produced, and second time intervals when imaging is performed. The improvement of the invention involves producing at least one actual spectrum of the Doppler signal, based upon Doppler samples produced during one of the first time intervals. A synthetic spectrum is then produced for an adjacent second time interval, based upon the actual spectrum. The synthetic spectrum is then converted into a corresponding time domain data set, and the audio signal for the second time interval is then produced based upon the time domain data set. At least some of the points of the synthetic spectrum preferably include a randomly selected phase factor, to reduce echo artifacts and other modulation effects.

20 Claims, 3 Drawing Sheets

SPECTRAL INTERPOLATION OF ULTRASOUND DOPPLER SIGNAL

FIELD OF THE INVENTION

The present invention relates to medical ultrasound diagnostic devices and, in particular, to a medical ultrasound device that uses Doppler processing to determine the velocity of blood or other structures within a patient's body.

BACKGROUND OF THE INVENTION

Medical ultrasound scanners typically produce a two-dimensional image of a planar region of a patient's body. The image is created by transmitting a series of ultrasound pulses into the region under investigation, and receiving and processing the echoes of the transmitted pulses, to build up a two-dimensional image. Modern ultrasound scanners are capable of obtaining images at a fast enough rate, e.g., 20 or more times per second, so that a real time display of the region under investigation can be created on a video monitor.

In recent years, ultrasound devices have been improved by adding the capability of obtaining Doppler information from a selected sample volume within the two-dimensional region under investigation. The Doppler data represents the velocity of structures within the selected volume. Thus if the selected volume is within a blood vessel, data can be obtained concerning blood velocity. Such data can be extremely useful in diagnosing various cardiac and other circulatory system problems.

Typically, the Doppler data is produced in both video and audio forms. The video form of the Doppler data consists of a two-dimensional graph on a video display, the graph having time along the horizontal axis and frequency along the vertical axis. Each column of the graph represents the frequency spectrum of the Doppler signal at the corresponding point in time. Such a display is typically scrolled across the screen as new data is acquired. For audio output, the raw Doppler signal, having a frequency equal to the transmitted frequency plus the Doppler modulation, is demodulated by removing the frequency of the transmitted signal, and the demodulated Doppler signal is then converted by a speaker into a corresponding audio signal. For most clinically significant cases, the frequency of the audio signal is within the range of human hearing, and thus can be used directly by an operator to sense blood flow patterns and other movement within the subject's body. An operator carrying out an investigation with the ultrasound scanner will often rely heavily on the information presented via the audio Doppler signal, in order to seek regions in the circulatory system in which more detailed measurement or imaging may be of interest. It is, therefore, very important that the audio Doppler signal not be substantially distorted.

The current generation of medical ultrasound scanners can typically operate in a "simultaneous" mode in which both image and Doppler data are collected and displayed apparently simultaneously, in real time. The data collection cannot be literally simultaneous, because the transmit burst length, focusing, and steering patterns used for image acquisition are different from those used for Doppler processing. Thus inherent limitations of beamformer and scanhead design require that the acquisition of image and Doppler data be time multiplexed. The multiplexing rate is made sufficiently high so that the image and Doppler data appear to be acquired simultaneously.

For image data, the multiplexing reduces the frame rate, sometimes to the point at which motion in the image no longer appears continuous. For Doppler data, the effects of multiplexing depend upon the particular multiplexing technique employed. A fundamental difference between imaging and Doppler measurement is that with imaging, only one pulse is needed in each beam direction to collect data for a given frame. For Doppler processing, on the other hand, one must obtain samples over a substantial period of time, in order to accurately estimate the frequency content of the Doppler signal. Thus the imaging function of an instrument can be interrupted without interfering significantly with the measurement, while Doppler measurements must be continuous for longer periods of time to obtain accuracy.

One form of multiplexing currently in use in connection with pulsed (as opposed to CW) Doppler simply alternates between image and Doppler pulses. For a given Doppler sample volume depth within the subject, this technique reduces the Doppler pulse repetition frequency by a factor of at least two. As a result, the maximum Doppler frequency (and therefore the maximum velocity) that can be unambiguously detected is also reduced by a factor of two. If the velocity exceeds this reduced maximum, aliasing will occur, and misleading results will appear in both the video and audio outputs. Pulse-by-pulse switching between image and Doppler modes may degrade the frame rate and pulse repetition frequency by a factor somewhat greater than two, because dead time will generally be required in order to avoid interference between the image and Doppler echoes.

Because of the difficulties in the alternating approach described above, it has become common to time multiplex image and Doppler pulses using larger time slices. For example, a series of image pulses are transmitted, for a time period sufficient to produce a single complete frame of the image to be displayed. A series of Doppler pulses are then transmitted, at whatever pulse repetition frequency is appropriate for the sample volume depth at which the Doppler data is to be collected. This technique can often be used with only minimal impact on the Doppler video output. However for Doppler audio output, such a technique, if uncorrected, results in modulation of the audio output at the interruption rate. Therefore to furnish an acceptable audio output, it is necessary to fill in the Doppler data during the time intervals in which image data is being acquired.

Prior Doppler fill-in techniques are described in U.S. Pat. Nos. 4,407,293 and 4,559,952. The prior art techniques, in general, are based upon the generation of a substitute signal that replaces the directly measured Doppler signal for audio and/or video output, during periods of time when the direct Doppler signal is unavailable. The substitute signal preferably has spectral properties close to those of the actual Doppler signal, and also produces audible sound close to that of the actual signal when fed to an audio output device. However some techniques provided in the prior art have not been capable of providing Doppler fill-in without perceptibly altering the audio output produced by the ultrasound scanner. In addition, the time domain techniques used in the prior art have generally lacked the flexibility needed to tailor the fill-in to the characteristics of human hearing.

SUMMARY OF THE INVENTION

The invention provides a method and apparatus for producing the Doppler audio output in a medical ultrasound system. The invention is particularly applicable to a medical ultrasound system that can operate in a "simultaneous" mode in which both Doppler (pulsed or CW) and imaging data are acquired in an apparently simultaneous manner in real time.

The present invention provides an improvement for Doppler medical ultrasound methods that include transmitting ultrasound energy into a body, receiving echoes produced by such energy and processing the echoes to produce a Doppler signal, converting the Doppler signal into an audio signal, and converting the audio signal into audible sound. The Doppler signal includes information representing the velocity of a target volume within the body, and typically comprises a time series of Doppler samples produced at a series of sample times. The transmitting and receiving steps alternate between first time intervals during which the Doppler signal is produced, and second time intervals during which the Doppler signal is generally absent.

The improvement to which the present invention is directed comprises first producing at least one actual spectrum of the Doppler signal, based upon the Doppler signal produced during one of the first time intervals. A synthetic spectrum of the Doppler signal is then produced for a second time interval adjacent to the first time interval, based at least in part upon the actual spectrum. The synthetic spectrum is converted into a corresponding time domain data set, and the audio signal for the second time interval is then produced based at least in part upon the time domain data set. Each spectrum typically comprises a plurality of points, each having a magnitude and a phase, and at least some points of the synthetic spectrum preferably include a randomly selected phase factor. The randomization prevents the production of echoes or other artifacts in the audible sound produced by the invention.

DETAILED DESCRIPTION OF THE INVENTION

Figure 1:
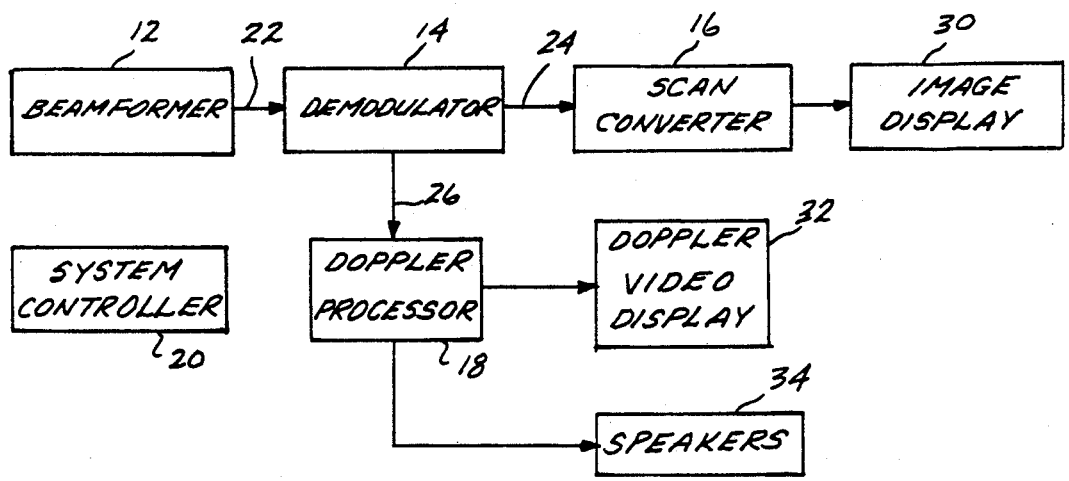
FIG. 1 is a block diagram of a medical ultrasound system in which the present invention may be used.

FIG. 1 presents a block diagram of a medical ultrasound system in which the present invention may be used. The system comprises beamformer 12, demodulator 14, scan converter 16, Doppler processor 18, and system controller 20. Beamformer 12 includes means for causing ultrasound energy to be transmitted into a patient's body, and for receiving echoes resulting from such transmitted energy. The beamformer may employ phased array, linear array, or mechanical scan techniques, and may utilize either analog or digital circuitry.

System controller 20 includes user interface means through which an operator of the system may place the system in imaging mode, Doppler mode, or simultaneous imaging/Doppler mode. In imaging mode, beamformer 12 produces RF signals on line 22 that represent the strengths of the ultrasound echoes received along a series of scanning lines through the patient's body. These RF signals are demodulated by demodulator 14, the demodulator essentially performing a detection function on the RF signal produced during imaging mode. The resulting demodulated image signal on line 24 is passed to scan converter 16. The scan converter accumulates echo data for a plurality of scan lines that make up a single frame. For a sector scan format, the scan converter also converts such data into a rectangular raster scan format. Successive frames are then displayed in real time on image display 30.

When the system is in Doppler mode, an operator sets the position of the sample volume from which the Doppler data is to be collected. For pulsed Doppler, the sample volume comprises a sample cell at a selected range, while for CW Doppler, the sample volume is cylindrical and extends along a scan line. Beamformer 12 then generates a series of echo signals from this sample volume, and produces the RF signals on line 22. Demodulator 14 converts the RF signals produced during Doppler mode to baseband or to an intermediate frequency, and produces demodulated in-phase (I) and quadrature (Q) signals on lines 26, the I and Q signals being collectively referred to as the "Doppler signal". The Doppler signal is received by Doppler processor 18, and processed to produce two outputs: a video output of the spectral characteristics of the Doppler signal, for display on Doppler display 32, and a two-channel audio output that is converted to audible sound by speakers 34.

Figure 2:
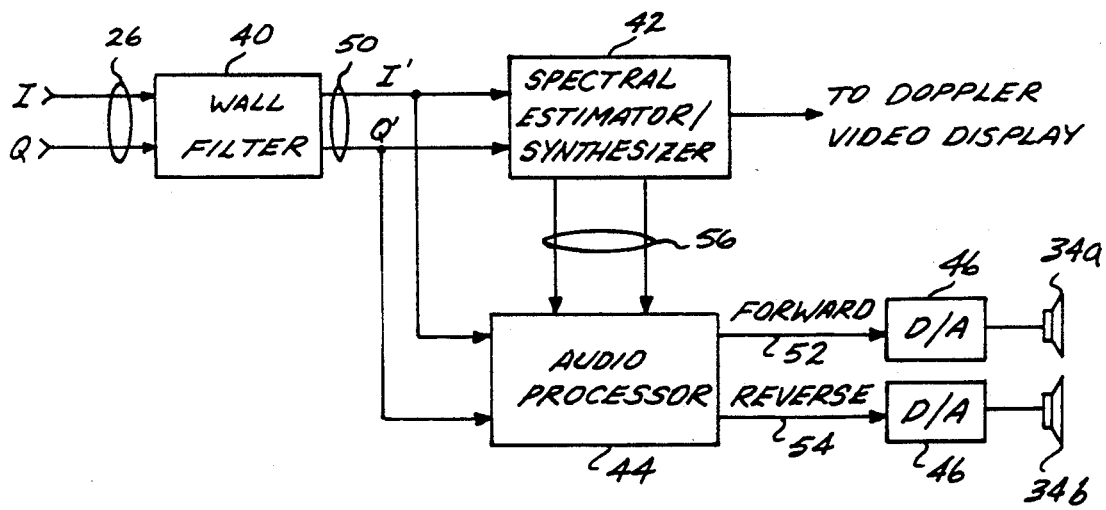
FIG. 2 is a block diagram of the Doppler processor.

Further details of Doppler processor 18 are shown in FIG. 2. The Doppler processor comprises wall filter 40, spectral estimator/synthesizer 42, audio processor 44, digital-to-analog (D/A) converters 46, and stereo speakers 34a and 34b that correspond to block 34 of FIG. 1. Wall filter 40 attenuates low frequency components from the Doppler signal. Such filtering is generally required because Doppler signals are often dominated by large reflections from stationary or slowly moving objects, such as the walls of blood vessels. Removal of these components by the wall filter permits the moving tissue of interest, e.g., blood within the vessel, to be detected more accurately.

The wall filter produces filtered signals I' and Q' on lines 50, and the I' and Q' signals are input to spectral estimator/synthesizer 42 and to audio processor 44. For simplicity, in the description that follows, the filtered signals I' and Q' will also be referred to as the "Doppler signal". Spectral estimator/synthesizer 42 periodically determines the frequency spectrum of the Doppler signal, and uses the frequency spectrum to produce the Doppler video display. Audio processor 44 processes the Doppler signal to produce forward and reverse signals on lines 52 and 54, respectively. By convention, the forward signal on line 52 represents velocities towards the ultrasound transducer, while the reverse signal on line 54 represents velocities away from the ultrasound transducer. D/A converters 46 convert the forward and reverse signals into analog form, for use by respective speakers 34a and 34b. The D/A converters would of course not be needed in an analog system. FIG. 2 also shows lines 56 connecting spectral estimator/synthesizer 42 to audio processor 44. This connection represents a signal path utilized for the purpose of the present invention, as further described below.

The spectral interpolation technique of the present invention is particularly applicable to an ultrasound system that is capable of operating in a "simultaneous" mode in which both image and Doppler data are collected and displayed in an apparently simultaneous manner. As previously described, such a system operates by alternating between Doppler and imaging time slices, in a manner generally illustrated by FIG. 3. Doppler data is collected during Doppler intervals 60, while image data is collected during generally shorter imaging intervals 62. Each Doppler interval 60 is at least long enough to permit one frequency spectrum to be determined, and each imaging interval 62 is preferably long enough to collect one full frame of image data. Thus for image display 30, the frame rate will be determined by the number of imaging intervals 62 per second. As long as this rate is on the order of 20 per second or greater, an acceptable real time image will be produced. For the Doppler display, it will be possible to determine and display at least one frequency spectrum for each Doppler interval 60, and in general it will be possible to produce an acceptable Doppler display on this basis.

Figure 3:
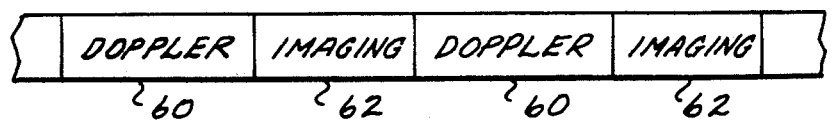
FIG. 3 is a diagram indicating alternate imaging and Doppler intervals.

The present invention is directed to the effect caused by the time multiplexing scheme shown in FIG. 3 on the audio Doppler output. In particular, the Doppler audio output will be unavailable whenever an imaging interval 62 occurs, and such periodic interruptions will lead to a distorted and unacceptable audio output. To correct this, the present invention generates a synthetic Doppler signal during the imaging intervals.

Figure 4:
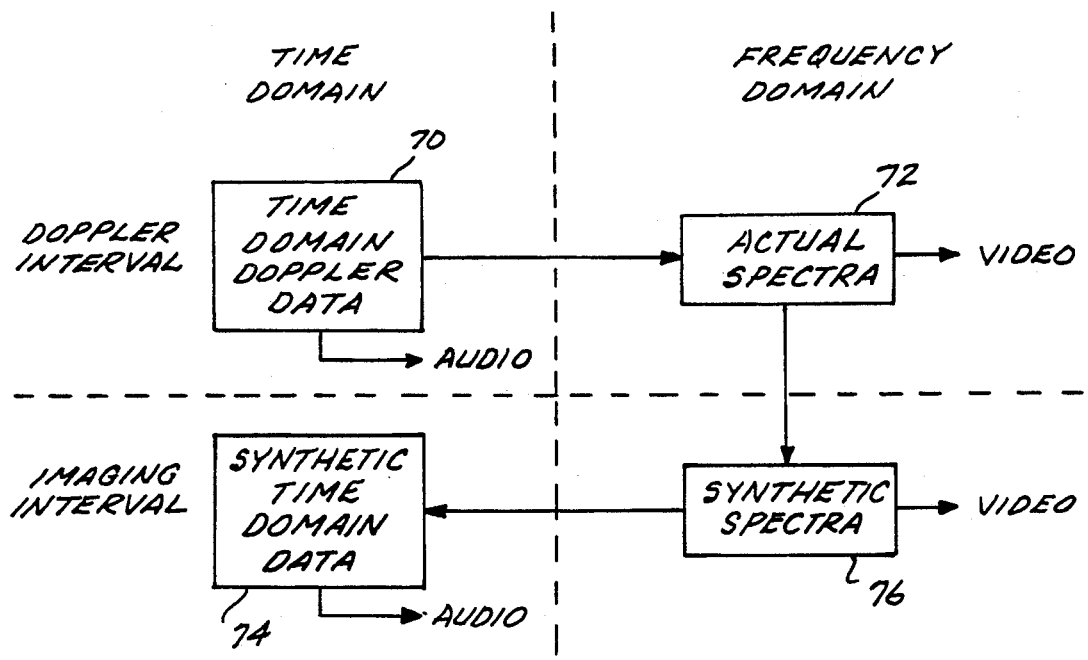
FIG. 4 is a diagram illustrating the generation of synthetic time domain data.

Referring to FIG. 4, blocks 70 and 72 represent operations carried out by the Doppler processor during a Doppler interval 60, while blocks 74 and 76 represent operations carried out during the subsequent imaging interval 62. The left-hand side of FIG. 4, comprising blocks 70 and 74, represent time domain operations or data, while the right-hand side of FIG. 4, comprising blocks 72 and 76, comprises frequency domain data or operations. During the Doppler interval, the time domain Doppler signal is available from the wall filter on line 50 (FIG. 2). This time domain Doppler signal is utilized directly by audio processor 44 to produce the audio output. To produce video output, the time domain Doppler signal is converted into the frequency domain by spectral estimator/synthesizer 42, as indicated in block 72 in FIG. 4. The spectral estimator/synthesizer accomplishes this by performing a Fourier transform, or any other suitable spectral estimation technique such as maximum entropy estimation, on a selected segment of time domain data, to produce corresponding frequency domain data that comprises or represents the actual spectrum of the Doppler signal. For an analog system, the required spectral estimation can be performed by a surface acoustic wave (SAW) device.

When the Doppler interval ends and the subsequent imaging interval begins, the time domain Doppler signal is no longer available from the wall filter. Spectral estimator/synthesizer 42 then begins to generate synthetic Doppler signal spectra, based upon one or more actual spectra produced during the preceding (or subsequent) Doppler interval. Further details concerning the computation of the synthetic spectra are provided below. The synthetic spectra are used to produce the video output, in a manner identical to that used during the Doppler intervals. To produce the audio output, the synthetic spectra are subjected to an inverse transform, transforming the synthetic spectra into corresponding synthetic time domain data, as indicated in block 74. This synthetic time domain data is then provided to the audio processor via line 56 shown in FIG. 2. Suitable fade-in techniques are used at the transitions between Doppler and imaging intervals, to avoid the generation of artifacts.

The technique of the present invention is based upon the fact that while human hearing is extremely sensitive to amplitude and/or phase discontinuities, its sensitivity to rapid changes in spectral content is limited. In particular, an audio signal will be perceived as a continuous sound if its spectrum tracks the spectrum of the actual audio signal at least every 20 milliseconds. Thus the present invention is capable of producing a continuous audio output, without perceptible distortion, as long as imaging intervals 62 are limited to about 20 milliseconds in length. The time required to collect one full frame of image data depends upon the imaging line density and the image depth. Should the time required to collect a full frame substantially exceed the 20 millisecond limit, then any number of options maybe used. First, the line density of the image can be reduced, so that a full frame can be collected within the 20 millisecond limit. A second option is to reduce the frame rate, such that less than a full frame of data is collected during each imaging interval, so that the length of the imaging interval stays under 20 milliseconds. A third option is to permit the imaging intervals to exceed the 20 millisecond limit. However, in general, as the imaging interval is lengthened beyond 20 milliseconds, audible distortions will gradually be introduced into the audio output. Therefore, in a preferred embodiment of the invention, the imaging intervals did not substantially exceed the 20 millisecond limit.

As stated above, the duration of each Doppler interval 60 is at least long enough to permit one actual frequency spectrum to be determined. This time is typically determined by two parameters: the time required for transients to die out in wall filter 40, and the number of time domain samples required for performing a spectral estimation. For example, in a digital implementation, if wall filter 40 is an M-point FIR filter, then the time required for transients to die out will be up to M sample points at the particular Doppler pulse repetition frequency. The number of points required to perform a spectral estimation will generally be based on the number of samples used by spectral estimator/synthesizer 42 to perform a Fourier transform or other spectral estimation technique on the Doppler signal. Thus if an N-point FFT is used, the minimum duration of Doppler interval 60 will be up to M+N samples. In most practical situations, the actual time duration will be considerably longer than this minimum.

Figure 5:
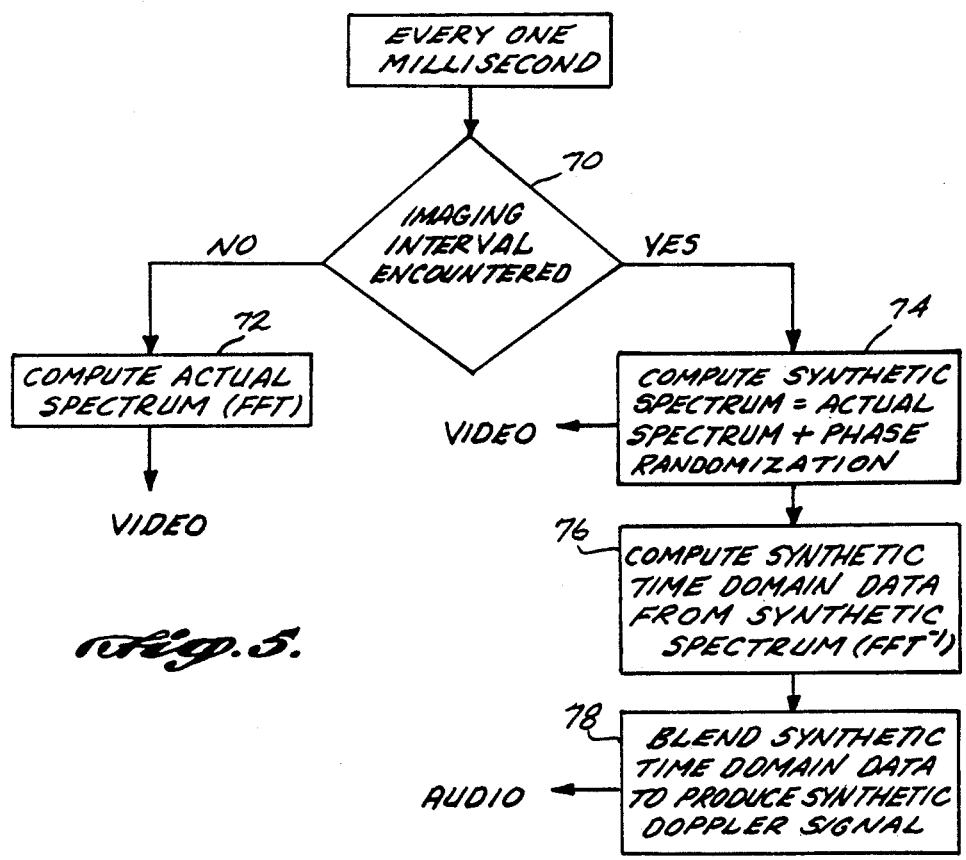
FIG. 5 is a flow diagram for the spectral estimator/synthesizer.
Figure 6:
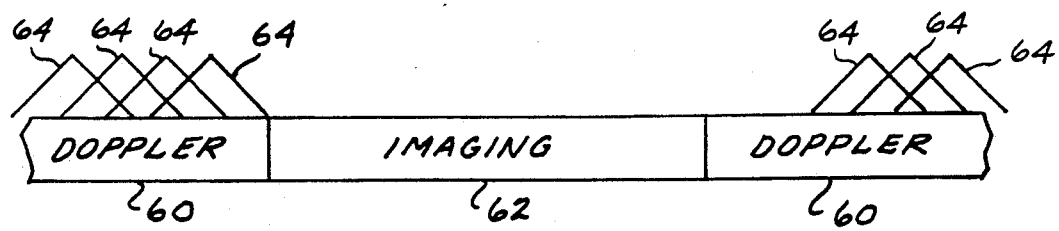
FIG. 6 is a diagram illustrating the production of actual spectra during Doppler intervals.
Figure 7:
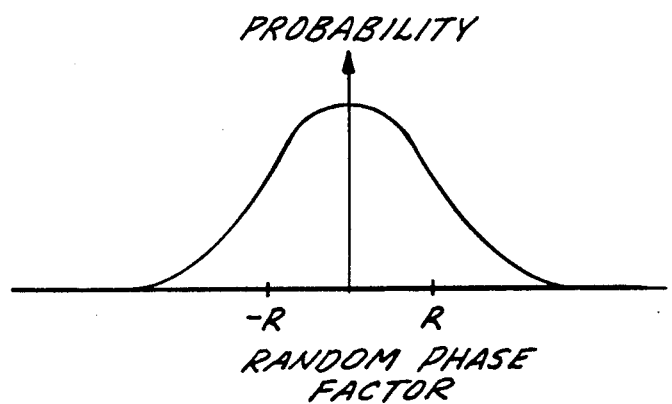
FIG. 7 is a graph of a preferred probability distribution for the random phase factor.

FIGS. 5–7 illustrate a preferred method by which spectral estimator/synthesizer 42 generates the synthetic Doppler signal on line 56 for use by the audio processor. The actual Doppler signal on line 50 is received and stored by the spectral estimator/synthesizer. Periodically, e.g., every one millisecond, the spectral estimator performs an analyze/synthesize cycle that is outlined in FIG. 5. The spectral estimator/synthesizer first determines, in block 70 whether the ultrasound system is in a Doppler or imaging interval. If the system is in a Doppler interval, then the spectral estimator/synthesizer computes an actual spectrum (block 72) based upon a predetermined number of the most recent samples of the Doppler signal, and forwards the actual spectrum to the Doppler video display. The actual spectrum may be determined by means of an FFT algorithm, or any other spectral estimation procedure. Each actual spectrum is preferably a "complex" spectrum, the term "complex" referring to the fact that there are two numbers associated with each sample or point in both the time and frequency domains. In the time domain, these two numbers correspond to the I and Q components of the Doppler signal. In the frequency domain, the pair of numbers may be taken to be the magnitude and phase of the spectrum of the Doppler signal at a particular frequency.

As is conventional in ultrasound Doppler processing, each set of time domain samples of the Doppler signal is preferably weighted by a suitable window prior to applying the FFT, in order to avoid the introduction of artifacts into the frequency spectrum. Referring to FIG. 6, lines 64 schematically represent the windows used for each FFT calculation. In practice, a Hanning window will typically be preferable to the illustrated triangular windows. The rate at which the actual spectra are determined and the time interval covered by each FFT calculation are preferably adjusted such that the sets of Doppler samples used to compute successive actual spectra substantially overlap one another. The actual spectra are stored by the spectral estimator/synthesizer in a memory (e.g., RAM), and used in a conventional manner to produce the Doppler display during each Doppler interval. During such Doppler intervals, the Doppler signal on line 50 is directly received by audio processor 44, and used by the audio processor to generate the forward and reverse signals for driving speakers 34.

If the spectral estimator/synthesizer determines in block 70 that an imaging interval has been encountered, then the spectral estimator/synthesizer switches to synthesize mode, commencing with block 74. In synthesize mode, the spectral estimator will produce synthetic spectra for use in generating the Doppler display, and will also produce a synthetic time domain Doppler signal on line 56 for use by audio processor 44 in place of the actual Doppler signal on line 50, since the latter is unavailable during an imaging interval. In accordance with the present invention, the first step in producing the synthetic (time domain) Doppler signal is to compute a synthetic spectrum (block 74) based on one or more actual spectra. The synthetic spectrum is forwarded to the Doppler video display. Preferred techniques for computing the synthetic spectra are described below. Block 76 then converts the synthetic spectrum into a synthetic time domain data set, using for example an inverse FFT procedure. The synthetic time domain data set is then blended with other synthetic time domain data sets, and/or with the actual Doppler signal on line 50 at the beginning and end of each imaging interval, to produce the synthetic Doppler signal on line 56 for use by the audio processor.

In the simplified procedure diagrammed in FIG. 4, the spectral estimator/synthesizer executes block 72 during a Doppler interval at the same rate (1,000 Hz) that it executes blocks 74, 76 and 78 during an imaging interval. However in general, these rates need not be identical, and can be varied from one another to optimize a particular application.

Referring to FIGS. 3 and 6, at the end of imaging intervals 62, samples of the Doppler signal are once again available on line 50. However, as described above, a predetermined number of samples will generally be required in order to eliminate transients produced in wall filter 40. Thus, the Doppler processor does not revert to Doppler mode until the required number of transient free samples are available. Thus, for example, for an M-point FIR wall filter and an N-point FFT, the Doppler processor does not return to Doppler mode until M+N samples of the Doppler signal have been produced.

The synthetic spectra computed in block 76 are based upon one or more actual spectra computed during the preceding and/or following Doppler intervals. For example, the synthetic spectra can be based upon the last actual spectrum determined before the imaging interval, upon the average of two or more actual spectra determined before the imaging interval, or based upon a first or higher order interpolation of the actual spectra determined before and after the imaging interval. The first of these approaches is the simplest, and has been found to give excellent results. For this technique, the spectral/synthesizer estimator needs to save only a single actual spectrum in a suitable memory, and that spectrum can then be used throughout the subsequent imaging interval to compute a series of synthetic spectra. On the other hand, interpolation using before and after spectra will in general produce fewer artifacts, at the cost of greater system complexity.

If each synthetic spectra computed during an imaging interval was simply equal to the last preceding actual spectrum, then all synthetic spectra for the imaging interval would be identical. Therefore each synthetic time domain data set produced during a given imaging interval would be the same. The result would be a generally unacceptable echo heard in the audio output of the system. Therefore to eliminate this effect, each synthetic spectrum is preferably subjected to a phase randomization process. In particular, each synthetic spectrum is computed by starting with the actual spectrum, and then randomly varying the phase of each point in the actual spectrum, while leaving the magnitude of each point unchanged. The result is a synthetic spectrum that has the same magnitude as the actual spectrum, but different phase. Because the randomization process is different for each synthetic spectrum, the synthetic time domain data sets are no longer identical to one another, and the echo effect is eliminated.

There are a number of suitable techniques for carrying out the phase randomization process. In the simplest technique, the phase of each point in each synthetic spectrum is simply set equal to a random number in the interval 0 to $2\pi$. However, in general, it has been found that the resulting wide variation in the phase between adjacent synthetic spectra produces artifacts in the audio output. Therefore in a preferred technique, the phase of each synthetic spectrum point is set equal to the phase of the corresponding actual spectrum point, plus a randomly selected phase factor substantially less than $2\pi$. For example, FIG. 7 plots random phase factors on the horizontal axis, and the probability of selecting each such factor on the vertical axis. The probability distribution is Gaussian, with a standard deviation of R. If parameter R is too small, then very little phase randomization occurs, and echoes result. On the other hand, if parameter R is too large, discontinuities are heard in the audio output. It has been found that a preferred range for R is about $\pi/10$ to $\pi/2$ radians. Another suitable randomization technique is to calculate each synthetic spectra by applying a phase randomization factor to the most recently computed synthetic spectra for the same imaging interval, rather than upon the last actual spectra.

It should be noted that in this context, the term "random" should be understood to include pseudo-random numbers, so long as each synthetic spectra is based upon a unique phase randomization factor. Furthermore, it is possible to reuse a given random sequence for producing the phase randomization factors, so long as the length of the random sequence is long enough so that no audible artifacts occur.

Figure 8:
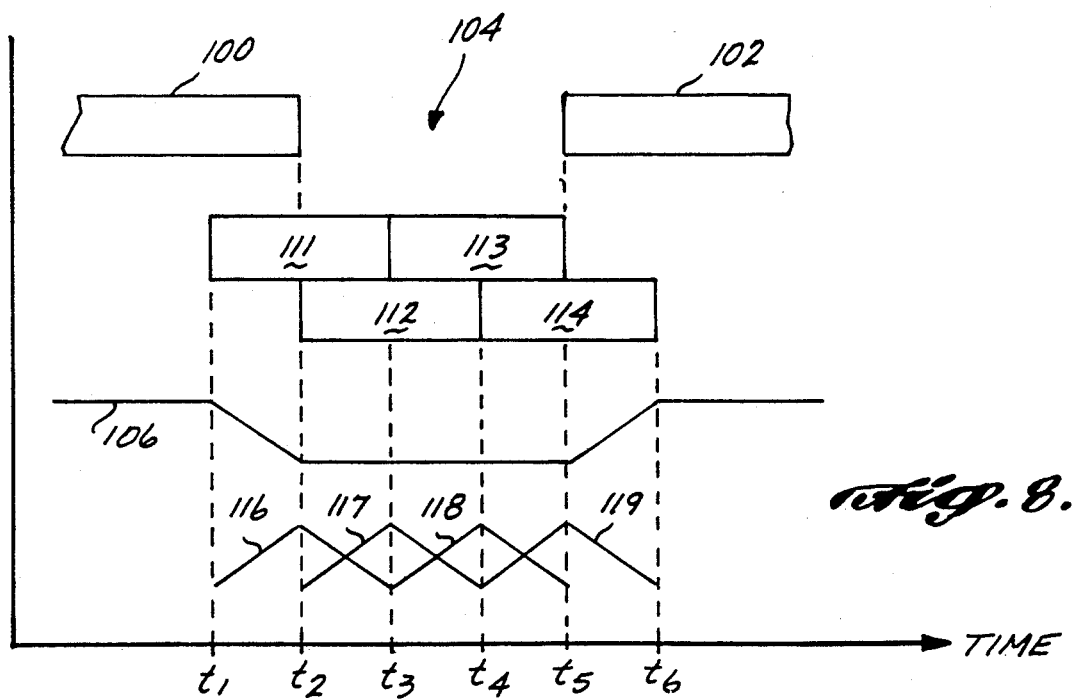
FIG. 8 is a diagram illustrating the blending of time domain data.

FIG. 8 diagrams a preferred technique for blending the synthetic time domain data sets with one another, and with the actual Doppler signal generated before or after the imaging interval, to produce the synthetic Doppler signal. Blocks 100 and 102 represent the actual Doppler data surrounding imaging interval 104. Blocks 111-114 represent four synthetic time domain data sets generated by the spectral estimator/synthesizer for imaging interval 104. This data is combined by a fade-in technique utilizing weighting function 106 for the actual Doppler data, and weighting functions 116-119 for data sets 111-114, respectively. The functions 106 and 116-119 are illustrated schematically, and in practice, Hanning or other non-triangular windows would typically be used. During time interval from $t_1$ to $t_2$, the synthetic Doppler signal is determined by averaging the data in blocks 100 and 111 in accordance with weighting functions 106 and 116, respectively. During time interval from $t_2$ to $t_3$, the synthetic Doppler signal is determined by averaging blocks 111 and 112, using weighting functions 116 and 117, respectively. To simplify the blending process, the length of imaging interval 104 is preferably set equal to a multiple of one-half of the duration of each synthetic time domain data set.

It has been found that for some applications, it may be desirable to produce the Doppler video display during the imaging intervals on the synthetic time domain data produced for that imaging interval. Thus to apply this technique, the synthetic time domain data would be produced for the imaging interval, using for example the technique shown in FIG. 8. Referring back to FIG. 4, this synthetic time domain data would then be converted to the frequency domain, using an FFT or another suitable procedure. The resulting frequency domain data would then be used to produce the Doppler video display for that imaging interval.

While the preferred embodiments of the invention have been described, variations will be apparent to those skilled in the art. Accordingly, the scope of the invention is to be determined by reference to the following claims.

The embodiments of the invention in which an exclusive property or privilege is claimed are defined as follows:

1. In a Doppler medical ultrasound method that includes transmitting ultrasound energy into a body, receiving echoes of the ultrasound energy and processing the echoes to produce a Doppler signal that includes information representing the velocity within the body, converting the Doppler signal into an audio signal, and converting the audio signal into audible sound, the transmitting and receiving steps alternating between first time intervals during which the Doppler signal is produced and second time intervals, an improved method for synthesizing the audio signal during the second time intervals, the method comprising:

producing at least one actual spectrum of the Doppler signal based upon the Doppler signal produced during one of the first time intervals;

producing a synthetic spectrum of the Doppler signal for a second time interval adjacent to said one first time interval, based at least in part upon said actutal spectrum;

converting the synthetic spectrum into a corresponding time domain data set; and producing the audio signal for the second time interval based at least in part upon said time domain data set.

2. The method of claim 1, wherein the Doppler signal comprises a time series of Doppler samples.

3. The method of claim 2, wherein each spectrum comprises a plurality of points, each point having a magnitude and a phase, and wherein at least some points of the synthetic spectrum include a randomly selected phase factor.

4. The method of claim 3, wherein the phase factor is selected from a range extending from approximately $-R$ to $+R$, where R is in the range of $\pi/10$ to $\pi/2$ radians.

5. The method of claim 1, wherein the second time interval immediately follows the first time interval.

6. The method of claim 1, wherein first and second actual spectra of the Doppler signal are produced based upon the Doppler signal produced during first time intervals preceding and following, respectively, the second time interval, and wherein the synthetic spectrum is produced based upon the first and second actual spectra.

7. The method of claim 1, wherein a plurality of synthetic spectra and corresponding time domain data sets are produced during each second time interval, and wherein the audio signal is produced by combining the time domain data sets.

8. The method of claim 7, wherein each spectrum comprises a plurality of points, each point having a magnitude and a phase, and wherein at least some of the points of each synthetic spectrum include a randomly selected phase factor, such that the time domain data sets differ from one another.

9. The method of claim 8, wherein the time domain data sets overlap one another, and wherein for each time during the second time interval, the audio signal is produced by averaging two or more overlapping time domain data sets.

10. The method of claim 9, wherein the first time domain data set produced during the second interval overlaps the Doppler signal produced during the preceding first time interval, and wherein the last time domain data set overlaps the Doppler signal produced during the subsequent first time interval.

11. In a Doppler medical ultrasound system that includes means for transmitting ultrasound energy into a body, means for receiving echoes of the ultrasound energy and processing the echoes to produce a Doppler signal that includes information representing the velocity of a target volume within the body, means for converting the Doppler signal into an audio signal, and means for converting the audio signal into audible sound that corresponds to the Doppler signal, the transmitting and receiving means alternating between first time intervals during which the Doppler signal is produced and second time intervals, improved means for synthesizing the audio signal during the second time intervals, said improved means comprising:

means for producing at least one actual spectrum of the Doppler signal based upon the Doppler signal produced during one of the first time intervals;

means for producing a synthetic spectrum of the Doppler signal for a second time interval adjacent to said one first time interval, based at least in part upon said actual spectrum;

means for converting the synthetic spectrum into a corresponding time domain data set; and means for producing the audio signal for the second time interval based at least in part upon said time domain data set.

12. The improvement of claim 11, wherein the Doppler signal comprises a time series of Doppler samples.

13. The improvement of claim 12, wherein each spectrum comprises a plurality of points, each point having a magnitude and a phase, and wherein at least some points of the synthetic spectrum include a randomly selected phase factor.

14. The improvement of claim 13, wherein the phase factor is selected from a range extending from approximately $-R$ to $+R$, where R is in the range of $\pi/10$ to $\pi/2$ radians.

15. The improvement of claim 11, wherein the second time interval immediately follows the first time interval.

16. The improvement of claim 11, wherein first and second actual spectra of the Doppler signal are produced based upon the Doppler signal produced during first time intervals preceding and following, respectively, the second time interval, and wherein the synthetic spectrum is produced based upon the first and second actual spectra.

17. The improvement of claim 11, wherein a plurality of synthetic spectra and corresponding time domain data sets are produced during each second time interval, and wherein the audio signal is produced by combining the time domain data sets.

18. The improvement of claim 17, wherein each spectrum comprises a plurality of points, each point having a magnitude and a phase, and wherein at least some of the pionts of each synthetic spectrum include a randomly selected phase factor, such that the time domain data sets differ from one another.

19. The improvement of claim 18, wherein the time domain data sets overlap one another, and wherein for each time during the second time interval, the audio signal is produced by averaging two or more overlapping time domain data sets.

20. The improvement of claim 19, wherein the first time domain data set produced during the second interval overlaps the Doppler signal produced during the preceding first time interval, and wherein the last time domain data set overlaps the Doppler signal produced during the subsequent first time interval.

* * * * *